United States Patent [19]
Dave et al.

[11] Patent Number: 5,476,951
[45] Date of Patent: Dec. 19, 1995

[54] SYNTHESIS OF TRINITROAZETIDINE COMPOUNDS

[76] Inventors: Paritosh R. Dave, 1 Rustic Ridge Rd., Apt. A37, Little Falls, N.J. 07424; Theodore Axenrod, 101 Chestnut St., Englewood Cliff, N.J. 07632

[21] Appl. No.: 67,553

[22] Filed: May 26, 1993

[51] Int. Cl.[6] ................................................. C07D 205/04
[52] U.S. Cl. ...................................................... 548/953
[58] Field of Search ............................................. 548/953

[56] References Cited

PUBLICATIONS

Archibald, T. G. et al, "Synthesis and X–Ray Crystal Structure of 1,3,3–Trinitroazetidine" J. Org. Chem. 55 No. 9 (1990) pp. 2919–2924.
Oyumi, Y. et al "Crystal Structure and Molecular Dynamics . . . " J. Phys. Chem. (1985), 89, 4317–4324.
Chemical Abstracts 105: 78351w (1986).
March, J. Advanced Organic Chemistry, McGraw–Hill, N.Y., p. 675, (1968).

*Primary Examiner*—Jacqueline Haley

[57] ABSTRACT

Method of synthesizing a 1,3,3 trinitroazetidine compound (TNAZ) comprising the steps of:
selecting a compound of the formula I:

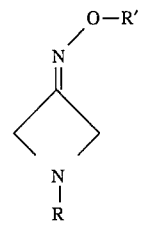

wherein R' is one of hydrogen and an organic group and R is selected from the group consisting of electron withdrawing and electron donating groups; and,
reacting the selected compound with a nitrolyzing agent such that a TNAZ compound is formed from the reaction.

14 Claims, No Drawings

SYNTHESIS OF TRINITROAZETIDINE COMPOUNDS

BACKGROUND OF THE INVENTION

The present invention relates to the synthesis of trinitroazetidine (TNAZ) compounds and, in particular, to 1,3,3 TNAZ. The invention further relates to novel compounds useful as intermediates in the synthesis of 1,3,3 TNAZ and novel methods for synthesizing such compounds.

SUMMARY OF THE INVENTION

Prior attempts to manufacture TNAZ, a known compound having high energy content, involve the carrying out of a series of multiple reactions designed to achieve substitution of three nitro groups at the 1 and 3 positions of an azetidine ring structure, Archibald et al., *J. Org. Chem.* 1988, 53, 4645. Each step in the reaction sequence produces unwanted side products, requires purification of desired intermediate products and provides very low yield of the desired TNAZ end product. Such prior processes are time consuming and so costly as to be commercially unfeasible.

The present invention provides a simple, high yield process for making 1,3,3 TNAZ from certain compounds which can be converted to 1,3,3 TNAZ in a simple, one-step, high yield reaction. Those compounds which can be converted in one step to produce 1,3,3 TNAZ in high yield according to the invention have the following general formula:

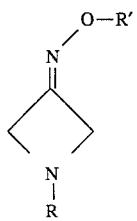

wherein R' is hydrogen or an organic group such as saturated or unsaturated organic radicals which may be substituted with one or more non-reactive substituents, carbonyl radicals such as R"—CO— or R"—OCO— or R"—NHCO—, or a sulfonyl radical such as R"—SO$_2$— where R" is an alkyl or aryl containing group which is branched, straight chain, cyclic, unsubstituted and/or substituted with one or more non-reactive groups. Typical R' groups are H, CH$_3$, C$_2$H$_5$, C$_3$H$_7$, COCH$_3$, COC$_2$H$_5$, CH$_2$C$_6$H$_5$, COOCH$_3$, COOC$_2$H$_5$, CONHC$_6$H$_5$, SO$_2$CH$_3$, SO$_2$C$_2$H$_5$, SO$_2$C$_6$H$_5$, SO$_2$-toluene and the like. The term "non-reactive" group or substituent as used herein means any conventional non-reactive substituent such as a hydrocarbon, halogen, nitroxy (e.g. NO$_2$ or NO$_3$), sulfoxy (e.g. SO$_2$ or SO$_3$), alkyl, aryl or organic oxy (e.g. alkoxy or aryloxy), which does not interfere with the primary reaction involved in obtaining the desired end product.

In general terms, R' may be a radical defined as follows:

TABLE I

| R' group Formula | Description |
|---|---|
| R$_1$ | hydrogen or an unsubstituted organic radical (e.g. C$_3$H$_7$) or an organic radical substituted with one or more non-reactive substituents (e.g. CH$_2$C$_6$H$_4$Cl) |

TABLE I-continued

| R' group Formula | Description |
|---|---|
| R$_2$ | —COR$_1$, —COOR$_1$, —CON(R$_1$)$_2$ |
| R$_3$ | —SO$_2$R$_1$ |

The term "organic radical" as used herein means any carbon containing radical which does not interfere with the primary reactions discussed below. Typical organic radicals are branched or straight chain alkyls, cycloalkyls, aryls and the like which may, in turn, be substituted at any saturated or aryl carbon atom with a non-reactive substituent as defined above.

R$_1$ is preferably hydrogen, a saturated organic radical or an organic radical whose only unsaturated carbon atoms are aryl or carbonyl moieties. Most preferably R$_1$ is a hydrocarbon such as a branched or straight chain alkyl, an aryl, an alkyl substituted aryl or an aryl substituted alkyl hydrocarbon.

The R group of the formula I compound which is bonded to the azetidine ring nitrogen is preferably an organic radical having a carbon, carbonyl, sulfonyl, oxy or phosphonyl functionality bonded directly to the nitrogen atom in the ring. The carbon, carbonyl, sulfonyl, phosphonyl or oxy group bonded to the ring nitrogen atom may in turn be bonded to hydrogen, oxygen, nitrogen, or an organic group such as alkyl and aryl radicals which are branched, straight chain, cyclic, unsubstituted or substituted with one or more non-reactive substituents as defined above. Most preferably, R is a substituted or unsubstituted alkyl, benzyl, alkyl or aryl hydryl, alkyl or aryl sulfonyl, alkyl or aryl carbonyl, or alkyl or aryl oxy radical. Typical examples of suitable R groups are arylhydryls such as benzhydryl (CH(C$_6$H$_5$)$_2$), alkyl or aryl sulfonyls such as methanesulfonyl and toluenesulfonyl, alkyls such as t-butyl and isobutyl and carbonyls such as acetyl, benzoyl and carbomethoxy.

In general terms, the R group of a formula I compound which is useful in the novel process for synthesizing a 1,3,3 TNAZ compound may be defined as follows:

TABLE II

| R group | Description |
|---|---|
| R$_4$ | an unsubstituted organic radical (e.g. t-butyl, C$_6$H$_5$) or a substituted organic radical having one or more non-reactive substituents (e.g. CH(C$_6$H$_5$)$_2$) C$_6$H$_4$Cl, C$_3$H$_6$NO$_3$) |
| R$_5$ | —COH, —COR$_4$, —COOR$_4$, —CONHR$_4$, CON(R$_4$)$_2$ |
| R$_6$ | —SO$_2$R$_4$ |
| R$_7$ | —P—(OR$_4$)$_2$ $\parallel$ O |

R$_4$ is preferably, a saturated organic radical or an organic radical whose only unsaturated carbon atoms are aryl or carbonyl moieties. Most preferably R$_4$ is a branched or straight chain alkyl, aryl, alkyl substituted aryl or aryl substituted alkyl hydrocarbon.

Further according to the invention certain specific novel compounds which have the formula I are also provided. In particular the invention provides novel compounds having the formula I wherein R is (a) an alkyl radical such as methyl, ethyl, isobutyl, t-butyl or the like, the organic portion of the alkyl radical being unsubstituted or substituted with one or more non-reactive substituents as defined above, (b) a carbonyl radical such as acetyl, benzoyl, carbomethoxy (COOCH$_3$), carbobenzoxy (COOC$_6$H$_5$), carbobenzyloxy (COOCH$_2$C$_6$H$_5$), carboamino (CONHR$_4$ or CON(R$_4$)$_2$) and the like, the organic portion of the carbonyl radical being unsubstituted or substituted with one or more non-reactive substituents as defined above, (c) a sulfonyl radical substituted with an organic group such as methanesulfonyl and t-butylsulfonyl, the organic portion of the sulfonyl radical being unsubstituted or substituted with one or more nonreactive substituents as defined above or (d) a phosphonyl group

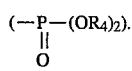

These compounds are novel as such and the R group of such novel compounds can be defined as follows:

TABLE III

| R group | Description |
| --- | --- |
| R$_8$ | an unsubstituted organic radical (e.g. C$_3$H$_7$, C$_5$H$_{11}$, C$_6$H$_5$) or a substituted organic radical, other than benzylaryls (CH$_{0-2}$—aryl$_{1-3}$), having one or more non-reactive substituents (e.g. C$_6$H$_4$Cl, C$_3$H$_6$NO$_3$). |
| R$_9$ | —COH, —COR$_4$, —COOR$_4$, —CONHR$_4$ —CON(R$_4$)$_2$ |
| R$_{10}$ | —SO$_2$R$_4$, other than —SO$_2$—aryl |
| R$_{11}$ | —P(OR$_4$)$_2$<br>‖<br>O |

Preferably R$_8$ is a saturated organic radical or an organic radical whose only unsaturated carbon atoms are aryl or carbonyl moieties. Most preferably R$_8$ is a hydrocarbon such as a branched or straight chain alkyl, an aryl, an alkyl substituted aryl or an aryl substituted alkyl hydrocarbon.

The invention further provides a novel method for synthesizing such compounds according to the following routine:

Scheme I

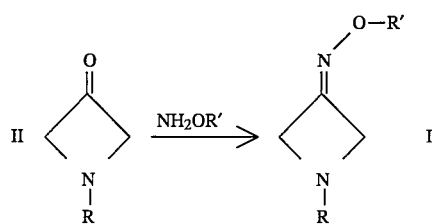

As the above reaction scheme I demonstrates, an N-substituted azetidin-3-one compound II is first selected, and the compound II is then converted to the imine (or oxime) derivative compound I by reacting the selected compound II with hydroxyl amine or NH$_2$OR' where R' is a radical as defined above in Table I. The conversion reaction of compound II to compound I is carried out in a suitable solvent which enables iminization of the ketone group. Typical solvents are polar solvents such alcohols (e.g. methanol, ethanol, glycols and the like), ethers (e.g., diethyl ether), THF and the like. A base material is typically included in the reaction mixture such as an acetate salt, a carbonate or bicarbonate salt, hydroxide salt and the like. The reaction mixture is preferably refluxed under mild conditions at the boiling point of the selected solvent, then cooled, the organic phase concentrated, washed with water and the organic phase separated by extraction.

The 3-azetidinone compound II may itself be prepared by a cyclization reaction of a selected ketone or hydroxy compound having a halo atom on one carbon atom alpha to the keto or hydroxy carbon and a nitrogen atom bonded to another carbon atom alpha to the keto or hydroxy carbon atom according to one or more of the following routines where X is a halide such as Cl, Br, I:

Scheme II

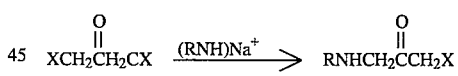

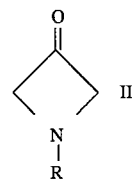

Scheme III

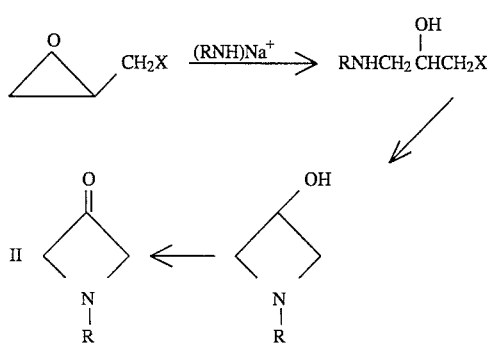

Similarly the 3-azetidinone compound II may be prepared by cyclization of a keto compound having a diazo function at one carbon alpha to the keto carbon and a nitrogen atom bonded to another carbon atom alpha to the keto carbon atom.

Scheme IV

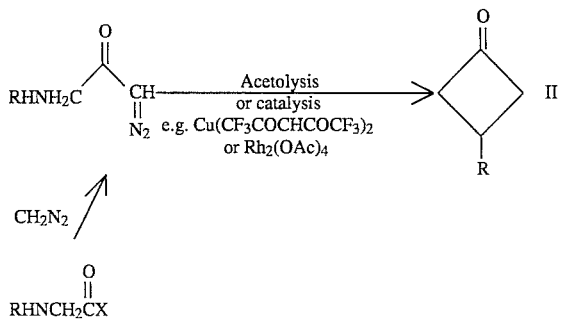

The formula I compounds can be converted in one step by the novel process according to the invention in high yield to 1,3,3 TNAZ by the following reaction:

Typical preparation and cyclization reactions of such diazocompounds are described in:

A. Pusino, A. Saba, G. Desole, V. Rosnati, Gazz. Chimica Italiana 115, 33 (1985); M. P. Moyer, P. L. Feldman, H. Rapoport, J. Org. Chem. 50, 5223 (1985); and O. V. Isakova, A. M. Sipyagin, V. V. Kartsev, Zhurnal Organicheskoi Khimii, 17, 1522 (1981).

Scheme V

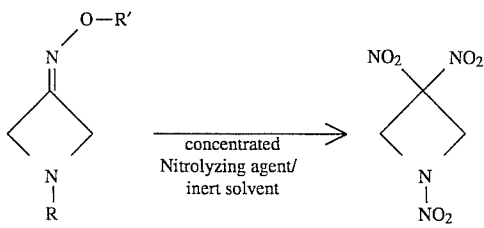

Preferred nitrolyzing agents for use in the conversion of compound I to TNAZ are $HNO_3$, $N_2O_4$, $N_2O_5$, $P_2O_5/HNO_3$, $Ac_2O/HNO_3$, $(CH_3)_3Si-ONO_2$, $NO_2BF_4$ and $NO_2SbF_6$. The nitrolyzing agent is preferably used in highly concentrated form containing less than about 2% by weight water. The reaction is preferably carried out in a dry, inert solvent which does not interfere with substitution of nitro groups at the 1,3,3 positions on the azetidine ring such as methylene chloride, chloroform, alkane solvents (e.g. pentane, hexane and the like) and freons. The reaction can be facilitated by adding an oxidizing agent such as $H_2O_2$ or $O_3$ following addition of the nitrolyzing agent.

DETAILED DESCRIPTION OF PREFERRED EMBODIMENTS

Preparation of 3-oximido benzylsulphonylazetidine

A mixture of the prepared ketone, hydroxylamine-HCl (2 equivalents) and sodium acetatetrihydrate (6 equivalents) in methanol is heated under reflux for two hours. The reaction mixture is cooled to room temperature and concentrated under reduced pressure. The residue is partitioned between water and methylene chloride. The organic phase is washed with saturated sodium bicarbonate solution, brine, and then dried (sodium sulfate) and filtered. The filtrate is concentrated under vacuum to yield the oxime.

1,3,3-Trinitroazetidine

A solution of 98% $HNO_3$, urea and ammonium nitrate is added to a refluxing solution of the prepared oxime in methylene chloride. Upon completion of the addition of the concentrated nitric acid solution, the mixture is heated at reflux for about 30 minutes and then cooled to room temperature. The cooled mixture is then poured over ice and the mixture allowed to separate into water and organic phases. The organic phase is separated, dried (sodium sulfate), filtered and concentrated under vacuum to yield 1,3,3 trinitroazetidine. Alternatively after the addition of nitric acid, 30% $H_2O_2$ is added dropwise until the blue green color disappears then worked up as described above.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

We claim:

1. Method of synthesizing a 1,3,3 trinitroazetidine compound (TNAZ) comprising the steps of:

selecting a compound of the formula I:

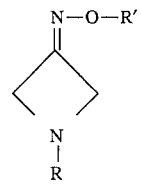

and, reacting the selected compound with a nitrolyzing agent such that a TNAZ compound is formed from the reaction;

wherein R' is a substituent selected from the group consisting of hydrogen, —$COR_1$, —$COOR_1$, —$CON(R_1)_2$, —$SO_2R_1$ and an organic radical which is unsubstituted or substituted said organic radical being selected from the group consisting of alkyl, aryl, benzyl and branched, straight chain and cyclic hydrocarbon radicals;

wherein R is selected from the group consisting of —$COR_1$, —$COOR_1$, —$CON(R_1)_2$, —$SO_2R_1$, —$PO(OR_1)_2$ and an organic radical which is unsubstituted or substituted said organic radical being selected from the group consisting of alkyl, aryl, benzyl, benzhydryl, and branched, straight chain and cyclic hydrocarbon radicals;

wherein $R_1$ is selected from the group consisting of hydrogen and an organic radical which is unsubstituted or substituted with a non-reactive moiety said organic radical being selected from the group consisting of alkyl, aryl, benzyl and branched, straight chain and cyclic hydrocarbon radicals.

2. The method of claim 1 wherein R is a hydrocarbon radical or an organic radical.

3. The method of claim 2 wherein R is selected from the group consisting of benzhydryl, toluenesulfonyl, t-butyl, methanesulfonyl, benzenesulfonyl, acetyl, benzoyl, carbomethoxy and $PO(OR_1)_2$.

4. The method of claim 1 wherein R' is selected from the group consisting of hydrogen and hydrocarbon radicals.

5. The method of claim 1 wherein the step of selecting comprises preparing the selected compound of formula I from a starting material having the formula II:

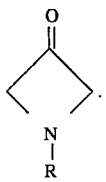

6. The method of claim 1 wherein the nitrolyzing agent is selected from the group of nitric acid, $N_2O_4$, $N_2O_5$, $P_2O_5/HNO_3$, $Ac_2O/HNO_3$, $(CH_3)_3Si-ONO_2$, $NO_2BF_4$ and $NO_2SbF_6$.

7. The method of claim 2 wherein the nitrolyzing agent is selected from the group of nitric acid, $N_2O_4$, $N_2O_5$, $P_2O_5/HNO_3$, $Ac_2O/HNO_3$, $(CH_3)_3Si-ONO_2$, $NO_2BF_4$ and $NO_2SbF_6$.

8. The method of claim 4 wherein the nitrolyzing agent is selected from the group of nitric acid, $N_2O_4$, $N_2O_5$, $P_2O_5/HNO_3$, $Ac_2O/HNO_3$, $(CH_3)_3Si-ONO_2$, $NO_2BF_4$ and $NO_2SbF_6$.

9. The method of claim 5 wherein the compound of formula I is prepared by reacting a selected starting material having the formula II with $NH_2OR'$.

10. The method of claim 5 wherein the nitrolyzing agent is selected from the group of nitric acid, $N_2O_4$, $N_2O_5$, $P_2O_5/HNO_3$, $Ac_2O/HNO_3$, $(CH_3)_3Si-ONO_2$, $NO_2BF_4$ and $NO_2SbF_6$.

11. The method of claim 5 wherein the starting material having the formula II is prepared by a cyclization reaction of one of a selected noncyclic ketone compound and a noncyclic hydroxy compound.

12. The method of claim 11 wherein the selected noncyclic ketone compound is selected from the group consisting of $RNHCH_2COH_2CX$ and $RHNH_2CCOCHN_2$ and wherein the noncyclic hydroxy compound is $RNHCH_2CH(OH)CH_2X$ and wherein X is a halogen radical.

13. The method of claim 9 wherein the starting material having the formula II is prepared by a cyclization reaction of one of a selected noncyclic ketone compound and a noncyclic hydroxy compound.

14. The method of claim 10 wherein the starting material having the formula II is prepared by a cyclization reaction of one of a selected noncyclic ketone compound and a noncyclic hydroxy compound.

* * * * *